(12) United States Patent
Liu

(10) Patent No.: US 7,363,828 B2
(45) Date of Patent: Apr. 29, 2008

(54) AEROSOL MEASUREMENT BY DILUTION AND PARTICLE COUNTING

(75) Inventor: Benjamin Y. H. Liu, North Oaks, MN (US)

(73) Assignee: MSP Corporation, Shoreview, MN (US)

( * ) Notice: Subject to any disclaimer, the term of this patent is extended or adjusted under 35 U.S.C. 154(b) by 2 days.

(21) Appl. No.: 11/211,376

(22) Filed: Aug. 25, 2005

(65) Prior Publication Data

US 2007/0242261 A1    Oct. 18, 2007

(51) Int. Cl.
*G01N 1/00*    (2006.01)

(52) U.S. Cl. ............................ 73/863.03; 356/436

(58) Field of Classification Search .......... None
See application file for complete search history.

(56) References Cited

U.S. PATENT DOCUMENTS

| | | | |
|---|---|---|---|
| 3,694,085 A | 9/1972 | Rich | |
| 3,806,248 A | 4/1974 | Sinclair | |
| 4,135,399 A * | 1/1979 | Kaczmarek et al. | 436/7 |
| 4,449,816 A | 5/1984 | Kohsaka et al. | 356/37 |
| 4,790,650 A | 12/1988 | Keady | 356/37 |
| 4,950,073 A | 8/1990 | Sommer | 356/37 |
| 5,026,155 A | 6/1991 | Ockovic et al. | 356/37 |
| 5,118,959 A | 6/1992 | Caldow et al. | 250/573 |
| 5,231,865 A * | 8/1993 | McDermott et al. | 73/28.04 |
| 5,239,356 A | 8/1993 | Hollander et al. | 356/37 |
| 5,519,490 A | 5/1996 | Nakata et al. | 356/338 |
| 5,903,338 A | 5/1999 | Mavliev et al. | 356/37 |
| 6,263,744 B1 * | 7/2001 | Russell et al. | 73/865.5 |
| 6,712,881 B2 | 3/2004 | Hering et al. | 95/228 |
| 6,829,044 B2 | 12/2004 | Liu | 356/37 |

* cited by examiner

*Primary Examiner*—Robert Raevis
(74) *Attorney, Agent, or Firm*—Westman, Champlin & Kelly, P.A.; Z. Peter Sawicki

(57) ABSTRACT

The present invention includes an apparatus for aerosol measurement having a high concentration of particles the apparatus comprising a diluter for diluting the concentration of particles in a sample aerosol stream to form a diluted aerosol stream, and a sensor for detecting the particles in the diluted aerosol stream by vapor condensation, droplet growth and optical detection. Such apparatus may be housed in a common housing along with the electronics for operating the apparatus and components such as pumps and filters that may be necessary. The diluter includes an input for an aerosol stream having an initial particle concentration, and a dilution stream. The aerosol stream and the dilution stream flow through a restriction which is sized such that turbulent flow is created so that the dilution stream and the aerosol stream are mixed to produce a diluted aerosol stream. The dilution stream is formed by drawing a portion from the diluted aerosol stream, filtering the portion to produce clean air that is mixed with the aerosol stream upstream from the restriction.

19 Claims, 5 Drawing Sheets

AEROSOL MEASUREMENT BY DILUTION AND PARTICLE COUNTING

BACKGROUND OF THE INVENTION

This invention relates to a method and apparatus for diluting an aerosol stream having a high particulate concentration so that subsequent particle measurement is more accurate. It also relates to the use of a diluter in combination with a Condensation Particle Counter (CPC) to measure aerosols at high concentrations.

Aerosols consisting of small particles suspended in air are widely encountered in nature and in the human environment. Techniques for aerosol measurement are important for studying the behavior of aerosols and their effect on the environment in which they occur. An important technique for aerosol measurement is the Optical Particle Counter (OPC). The instrument is also referred to as a Laser Particle Counter (LPC) if a laser light source is used for particle illumination. Another technique is the Condensation Particle Counter (CPC). Both techniques involve optical detection based on light-scattering, with the OPC detecting the particle by direct light scattering from the particle while the CPC detecting the particle by first condensing a vapor on the particle to form a droplet, which is then detected optically by light scattering or other techniques.

The lower detection of the OPC is generally on the order of 0.1 µm in particle diameter. Smaller particles can be detected by the OPC by using a stronger laser light source, a more sensitive photo-detector, or both, but the apparatus becomes increasingly more difficult to design and costly to manufacturer, making an alternative method of measurement preferred. An alternative device is the CPC that is capable of detecting particles as small as 0.002 µm in diameter. Very small particles can be detected by the CPC because a vapor is first condensed on the particles to form droplets of a larger size. The droplets are then detected optically by light scattering or other techniques.

Both the OPC and CPC are useful instruments for aerosol measurement with the CPC particularly useful for measuring small particles below the lower detection limit of the OPC, which is generally about 0.1 µm. Because of the potential health effect of small particles emitted by Diesel and spark ignition engines and other combustion sources, CPC is becoming increasingly important as a measuring instrument for engine exhaust particulate and similar measurements.

Historically the Condensation Particle Counter (CPC) is referred to as a Condensation Nucleus Counter (CNC) because the particles being detected form the nucleus of condensation in droplet formation. Both CPC and CNC are now used in the scientific and technical literature to refer to a measuring instrument based on vapor condensation, droplet growth and optical detection.

Both the CPC and the OPC have certain inherent limits on particle concentration. The count rate limit of a particle counter is exceeded when particles are passing through the light beam at too rapid a rate for the particles to be counted reliably by the detecting and counting circuitry. The coincidence counting limit is exceeded when more than one particle is present in the optical view volume of the detector causing light scattering from two or more particles to appear as one, leading to losses in particle counts. For high accuracy measurement both of these limits must not be exceeded.

For aerosol measurement by the CPC above the coincidence counting limit a photometric mode is often used. In the photometric mode, light scattering from the droplet cloud illuminated by the light beam is measured by the optical detector and used as a measure of droplet concentration. One commercial instrument using the photometric mode is the Model 3022A CPC from TSI, Inc. In this instrument, aerosols up to $\sim 10^4$ particles per cc are measured by single particle counting, while the photometric mode is used for high concentrations up to a maximum limit of $\sim 10^7$ particles per cc in concentration.

Since light scattering from a droplet cloud depends both on droplet size and droplet concentration, the photometric mode is less accurate than the single particle counting mode. In the photometric mode, a small variation in droplet size due to variation in vapor saturation and condensation conditions can cause the droplet size to change, giving rise to different instrument readings even if the aerosol concentration remains the same. A recent study shows that when several CPCs are placed in a side by side comparison, differences as much as 60% or more in the measured aerosol concentration can occur. ("Performance Evaluation of a Recently Developed Water-Based Condensation Particle Counter," S. Biswas, P. M. Fine, M. D. Geller, S. V. Hering and C. Sioutas, *Aerosol Science and Technology*, Vol. 39, pp. 419-427, 2005.) The photometric mode is believed to have contributed significantly to the observed discrepancy in the measured concentration.

SUMMARY OF THE INVENTION

Figure 1:
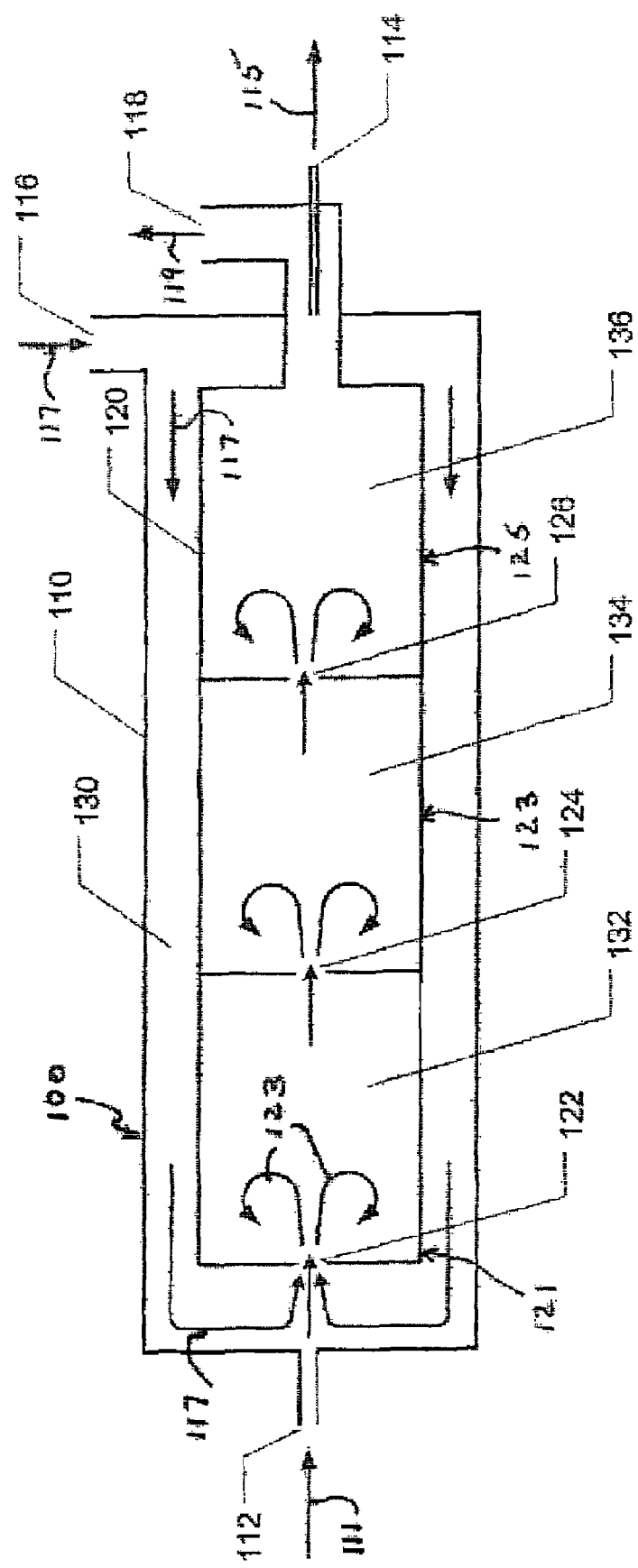
FIG. 1 is a schematic diagram of a high accuracy diluter of the present invention.

The present invention includes an apparatus for measuring an aerosol having a high concentration of particles the apparatus comprising a diluter for diluting the concentration of particles in a sample aerosol stream and a sensor for detecting the particles by vapor condensation, droplet growth and optical detection. Such apparatus may be housed in a common housing along with the electronics for operating the apparatus and accessory components such as pumps, filters, temperature and flow sensors, etc. that may be necessary.

The present invention also includes an apparatus and method for diluting an aerosol stream for subsequent counting of particles in the aerosol stream. The dilution apparatus allows an input aerosol stream having an initial particle concentration to be diluted by mixing with a clean air stream that is substantially free of particles. Mixing is accomplished by directing the aerosol stream and the clean air stream through a restriction which is sized such that turbulent flow is created downstream of the restriction causing the streams to mix to form a diluted stream of aerosol of a lower particle concentration.

The method includes providing a diluter for diluting a concentration of particles in the aerosol stream and detecting the particles by vapor condensation, droplet growth and optical detection. One embodiment of the method also draws a portion of the diluted aerosol stream, filters the portion so drawn to form a dilution stream of clean air substantially free of particles, and combines this dilution stream with the aerosol stream to thereby dilute the aerosol stream. In another aspect of the method, the aerosol and the dilution stream are drawn through a restriction, the restriction being sized such that turbulent flow is created downstream to mix the dilution stream and the aerosol stream.

In another aspect of this invention a plurality of such restrictions are positioned in series with each restriction sized to create turbulent flow to produce further mixing. The present invention also includes formation of the dilution stream by drawing a portion of the aerosol stream downstream of the restriction and filtering the drawn portion to produce the dilution stream substantially free of particles. A first pump may be used to draw the portion of the aerosol stream to produce the dilution stream free of particles. A second pump may also be used to draw the aerosol stream through the restriction or the series of restrictions.

In another aspect of the invention, a plurality of dilutors is connected in series such that the aerosol stream flows through each dilutor with each diluter drawing a portion of the diluted aerosol stream, filtering said portion and providing a dilution stream substantially free of particles to progressively dilute the aerosol stream.

DETAILED DESCRIPTION OF THE INVENTION

Like reference characters will be used to indicate like elements throughout the drawings.

As used herein, the terms below have the following meanings:

Aerosol is a gaseous medium containing suspended particles. The gaseous medium can be a pure gas, a gas mixture, such as air, with or without a vapor, such as a water vapor. For convenience all gaseous media are referred to as air. Clean air means air that is substantially free of particulate contaminants. The term, air, is often used to mean air with or without suspended particles when the particulate content of air is unimportant. Aerosol concentration is the concentration of particles in the aerosol, usually expressed in number of particle per cubic centimeter of air.

Pump is a device for moving air through a flow path to overcome the flow resistance of the path. The pump can be a rotary vane pump, a piston pump, or any other positive displacement pump. It can also be a blower with a rotating impeller for fluid movement, or any other fluid moving devices such as a vibrating diaphragm pump. For convenience all air movers are referred to as pumps. The pump is usually equipped with an electrical motor for pump rotation and the speed of the pump can also be adjusted, if desired to vary the flow rate.

Particle counter means a device for detecting and counting airborne particles. Particle counter includes an Optical Particle Counter (OPC) that detects particles optically by light-scattering or other optical techniques; a Laser Particle Counter (LPC), i.e. an OPC with a laser light source for particle illumination; and a Condensation Particle Counter (CPC), which is also known as the Condensation Nucleus Counter (CNC), a particle detecting device making use of vapor condensation, droplet growth, and optical detection.

Restriction is a restricted flow passageway for air to flow through at an increased velocity to create fluid turbulence for mixing or creating a pressure drop for flow measurement. The restriction can be an orifice, for example a hole in a plate; a nozzle, for example an orifice with a tapered entrance, or an entrance with varying cross-section and curved walls; a tube of a constant cross-section; or a capillary, a small diameter tube of a sufficient length to produce a pressure drop, generally for flow measurement purposes. For convenience, both the orifice and the nozzle are referred to as an orifice in this invention. The orifice can have a circular or non-circular cross-section, including such cross-sectional shapes as a straight or curved slit, an annulus, among others.

Housing means a structural framework, with or without an enclosure, on which components of an apparatus are mounted. Some of the components may be removed for mounting in a separate location for convenience and some may be mounted permanently elsewhere, again for convenience.

FIG. 1 is a schematic diagram of a high accuracy diluter 100 of this invention. The diluter 100 is a multi-stage turbulent jet diluter with a mixing-diluting first stage followed by one or more mixing stages downstream as will be described subsequently.

The high accuracy diluter 100 is suitable for reducing the particle concentration of an aerosol from a high level that exceeds the count rate limit or the coincidence counting limit of the particle counter discussed earlier to a sufficiently low level so that accurate particle counting can be made with the particle counter on the diluted aerosol stream.

The multi-stage turbulent jet mixer-diluter 100 includes an outer tube 110 of a generally cylindrical shape. The tube 110 has an inlet 112 to allow sample of an aerosol stream 111 to enter, an outlet 114 for a diluted aerosol sample 115 to exit, an inlet 116 for clean air 117 to enter for dilution and an outlet 118 for the excess diluted aerosol 119 to exit.

Inside the tube 110 is another cylindrical tube 120 having a first mixing diluting stage 121 with an orifice 122 as an inlet. Two optional mixing stages 123 and 125, each having orifices, 124 and 126 positioned downstream of stage 121. The mixing stages 123 and 125 also include chambers 134 and 136, respectively into which aerosol flows from the orifices 124 and 126. As the clean dilution air 117 enters the outer tube 110, it flows in the annular space between the tube 110 and tube 120. Upon reaching the end of the annual flow passageway, the clean dilution air 117 turns radially inward toward the orifice 122, where the clean dilution air meets the aerosol stream 111 entering the diluter through inlet 112 and joins the aerosol stream 111 to flow through the orifice 122. The size of orifice 122 is selected so that the airflow 123 out of the orifice forms a high velocity, turbulent jet. As this jet of air 123 enters the downstream chamber 132, its kinetic energy is dissipated by fluid turbulence causing the aerosol 111 and clean air 117 to mix. Mixing will cease when the kinetic energy of the flow is spent and dissipated by fluid turbulence.

Turbulent mixing of aerosol with clean air is usually incomplete in the first mixing-diluting stage 121 of the diluter. To enhance further mixing, the second mixing stage 123 and the third mixing stage 125 are provided. More mixing stages can be provided if necessary. For clarity and brevity, only two mixing stages are shown in addition to the first mixing-diluting first stage. The configuration shown in FIG. 1 is usually adequate to insure uniform mixing for most applications. Following mixing, the mixed and diluted aerosol then exits the diluter 100 through outlet 114 as a diluted aerosol sample, while excess aerosol, i.e. the remaining portion of aerosol, exits the diluter through outlet 118.

Figure 2:
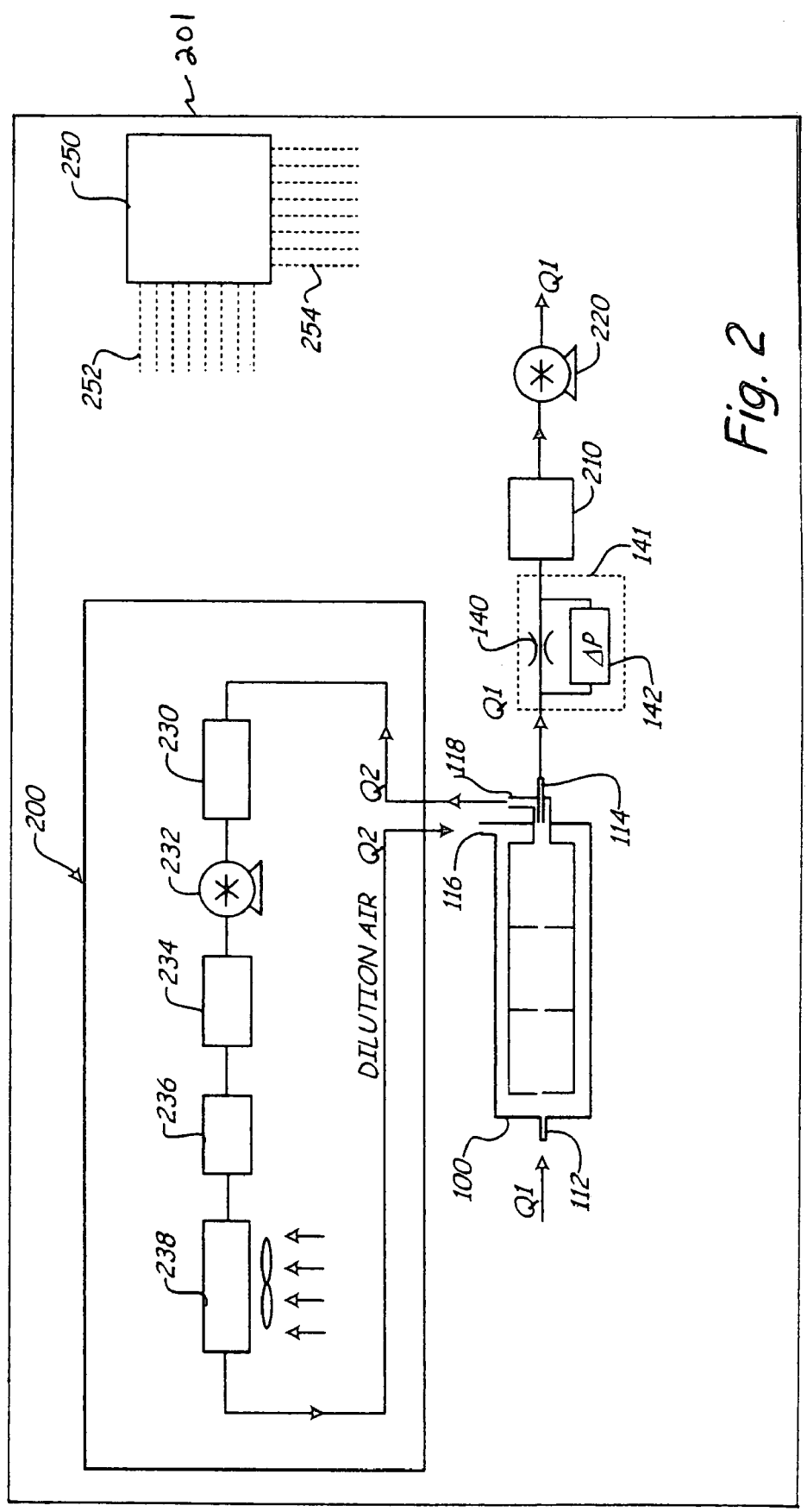
FIG. 2 is a schematic diagram depicting a single 3-stage turbulent-jet mixer-diluter with a recirculating clean air system drawing sample from the inlet and delivering a diluted sample at the exit to a condensation particle counter located downstream for counting particles in the diluted sample stream.

FIG. 2 shows a condensation particle counting system including a Condensation Particle Counter (CPC) 210, a diluter 100, and a recirculating flow system shown generally at 200 are disposed in a common housing 201 along with all electronic circuitry such as a controller, computer, and other specialized control circuitry to create a self-contained, small portable device that is user friendly and easy to operate and control.

Figure 3:
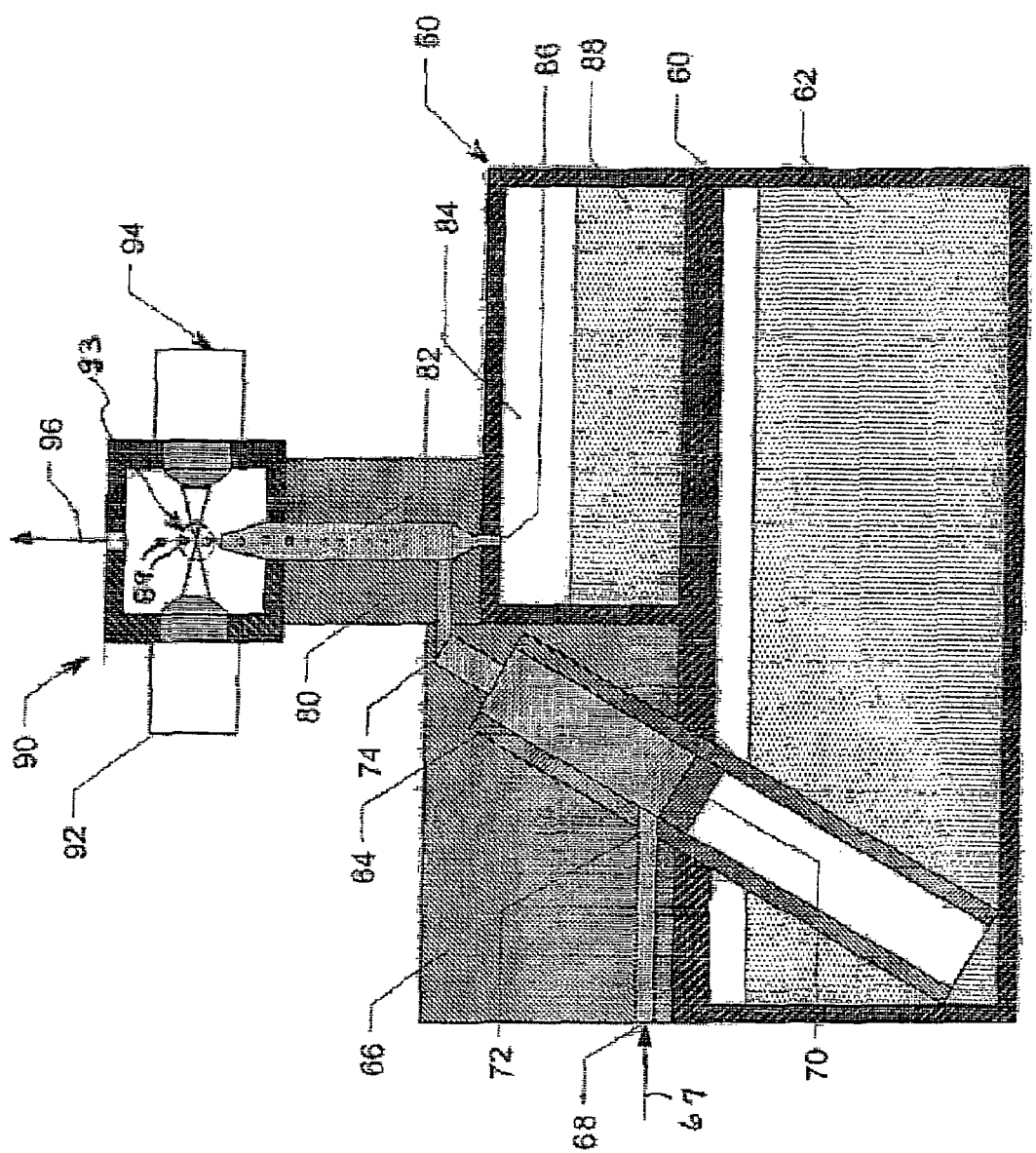
FIG. 3 is a schematic diagram depicting a condensation particle counter based on vapor condensation, droplet growth and optical detection for aerosol measurement.

FIG. 3 illustrates a CPC suitable for use in the present invention generally indicated at 50 similar to that described in U.S. Pat. No. 6,829,044 which is hereby incorporated by reference in its entirety. Combining the CPC with the diluter of the present invention, the CPC can be used for accurate single particle counting to measure aerosol concentration at high levels. Without a diluter, the CPC is usually limited to a concentration limit of approximately $0.5 \times 10^5$ particles per cc. Using a single diluter to reduce the aerosol concentration by a factor of 200, for instance, the CPC can be used for accurate concentration measurement up to about $10^7$ particles per cc. With two diluters connected in series, as described subsequently, accurate particle concentration up to $10^9$ particles per cc can be measured.

The CPC 50 includes a reservoir 60 containing a working fluid 62, such as butyl alcohol in liquid form. A porous metal tube 64 has its lower end in contact with working fluid 62 in the reservoir 60. By force of capillary surface tension, the fluid 62 enters interstitial pore space of porous metal tube 64 automatically, filling it with the working fluid 62. Part of the tube 64 is in thermal contact with a metal block 66, which is heated to a suitable temperature by an electric heater (not shown).

Aerosol 67 containing suspended particles to be counted enters the CPC 50 through an inlet 68 into a tubular passageway 72. As the aerosol flows through the tubular passageway 72, the aerosol becomes heated to nearly the same temperature as the metal block 66. The porous metal tube 64 is blocked by a solid blockage 70 just below the tubular flow passageway 72. The aerosol 67 enters the porous metal tube 64 through the tubular flow passageway 72 and begins to receive vapor from the working fluid that is being evaporated from the surface of the porous metal tube 64. As the aerosol flows out of the porous metal tube 64 through the passageway 74, the aerosol is saturated with vapor of the working fluid 62. The porous metal tube 64 is, therefore, also referred to as a saturator tube.

The aerosol 67 then flows through a tubular condenser 82 which is essentially a passageway in a metal block 80. The metal block 80 is kept at a low temperature by a thermoelectric cooler (not shown). As the aerosol flows through the condenser 82, the aerosol cools by rejecting heat to the colder walls of the condenser 82, causing the aerosol to become supersaturated with the working fluid vapor, leading to vapor condensation on particles to form droplets. As the aerosol continues its path in the condenser 82, the particles will grow as the droplet size increases. The droplets then flow out of the condenser 82 and into the optical sensor 90 for detection and counting by light scattering or other optical techniques. Some of the working fluid vapor will condense on the condenser walls, as well as water vapor, if present at a sufficiently high concentration. The condensed liquid on the walls of the condenser then flows under the influence of gravity through the small hole 86 at the bottom of the condenser 82 into the condensate reservoir 84 and collected there as a condensate 88.

An optical sensor 90 includes a light source 92, typically a solid-state laser, and appropriate lens and optics. Laser from the source 92 is focused to a small volume to increase the light's intensity in a high intensity illuminated region 93. As the droplets 89 pass through this high intensity, illuminated region, the optical view volume, they scatter light onto a detecting and sensing system 94. The output signal from 94 is processed electronically to provide data for determining the number of droplets passing through the laser beam. Following detection, the aerosol is then exhausted as indicated by arrow 96, usually by a pump (not shown) to the ambient.

Instruments for measuring particles in an aerosol based on vapor condensation and droplet growth followed by optical detection are referred to as condensation particle counters. Not all such prior art condensation particle counters (CPC) will have all the features described above and illustrated in FIG. 3, but all operate on substantially the same or a similar principle of vapor condensation, droplet growth and optical detection. Vapor condensation and droplet growth can occur by a heated saturator working in combination with a cold condenser. Vapor condensation and droplet growth can also occur by mixing a hot saturated vapor stream with a cold aerosol stream as described in U.S. Pat. No. 4,449,916, or by some other means. All such devices are referred to as CPCs, since the basic operating principles of the devices are substantially the same.

The recirculating flow system 200 as illustrated in FIG. 2 uses two pumps. One pump 232 provides clean air for dilution and another pump 220 maintains aerosol flow through the diluter 100 and the CPC 210.

Pump 232 draws a portion of flow at the required rate, Q2, from the diluted aerosol stream through the excess aerosol outlet 118 of the diluter, and passes the drawn portion through two high efficiency air filters, 230 and 234, one before pump 232 and one after; a flow sensor 236 and an air cooler 238 before returning the flow as clean dilution air at the same rate Q2 to the diluter though inlet 116. The clean dilution air is introduced upstream from the point where the air was withdrawn. Since flow is withdrawn and returned at the same rate to the diluter 100, there is no loss or gain in flow by the diluter 100 from the operation of the recirculating flow system 200. The flow drawn by pump 220 thus enters the diluter 100 as the sample flow rate Q1 and exits the diluter 100 at the same flow rate, Q1. The diluted aerosol sample at flow rate Q1 then enters a flow sensor 141 comprised of a flow restriction 140 and a differential pressure gage 142 and into CPC 210 for particle counting by the CPC.

The system 200 described above for withdrawing a portion of the diluted aerosol from the diluter and returning it as clean air for dilution after filtration provides a simple approach to flow management. The multiple streams of air flowing in and out of the diluter 100 must be managed properly. The task of managing such flows is generally quite complex. The diluter 100 allows a single flow sensor to be used for measuring the sample flow in and out of the diluter for particle counting by the CPC and a separate sensor for measuring the portion of aerosol drawn from the diluted aerosol stream and used as clean air for dilution. This approach significantly simplifies the flow measuring system, thereby reducing its cost and improving its accuracy.

To adjust the sample flow rate, Q1, the speed of pump 220 can be adjusted electrically. Alternatively the pump speed can be kept constant, and a manual or automatic throttle valve (not shown) can be use to vary the flow resistance to adjust the sample flow rate. Likewise, the clean air flow rate, Q2, can be adjusted by adjusting the speed of pump 232 electrically, or by keeping the pump speed constant and adjusting the flow rate by a manual or an automatic throttle valve, also not shown. For automatic flow control, the output of the two flow sensors in the circuit can be compared with the desired output according to set point values for the flow rates and adjusting the respective flow rates by adjusting the pump speed or by means of an automatic throttle valve until the desired set point values in flow rate have been achieved.

The system 200 also includes cooler 238 as illustrated in FIG. 2. The cooler 238 dissipates heat generated in the recirculating flow system 200 due to energy input from the pump 232 in maintaining the flow. The cooler 238 can be in the form of an air-to-air heat exchanger. Alternatively, a source of cooling fluid, such as water, can be providing for cooling. Other schemes for cooling the air are available and are well known to those skilled in the art of heat transfer and heating and cooling equipment design.

The diluter 100 and the particle counter used in the system need to be controlled accurately for aerosol measurement. An electronic controller 250 is provided to receive input from the flow sensors and provide appropriate control signal to maintain the required airflow rate through the system. A multitude of sensor input lines are shown at 252 to receive input from sensors used in the system and a multitude of output lines 254 are provided to deliver a control signal to the pumps to control their speed or automatic throttle valves, if used, to adjust the flow rates in the system, as well as other system components, such as heater, cooler, etc. that need to be controlled. The controller 250 can have both analog and digital control capabilities to allow the system to be controlled precisely and accurately for accurate particle counting by the CPC by software, firmware and hardware control schemes. In addition, the output signal from the CPC can be processes by appropriate signal processing circuitry in the controller 250 for data storage, analysis and display purposes.

Figure 4:
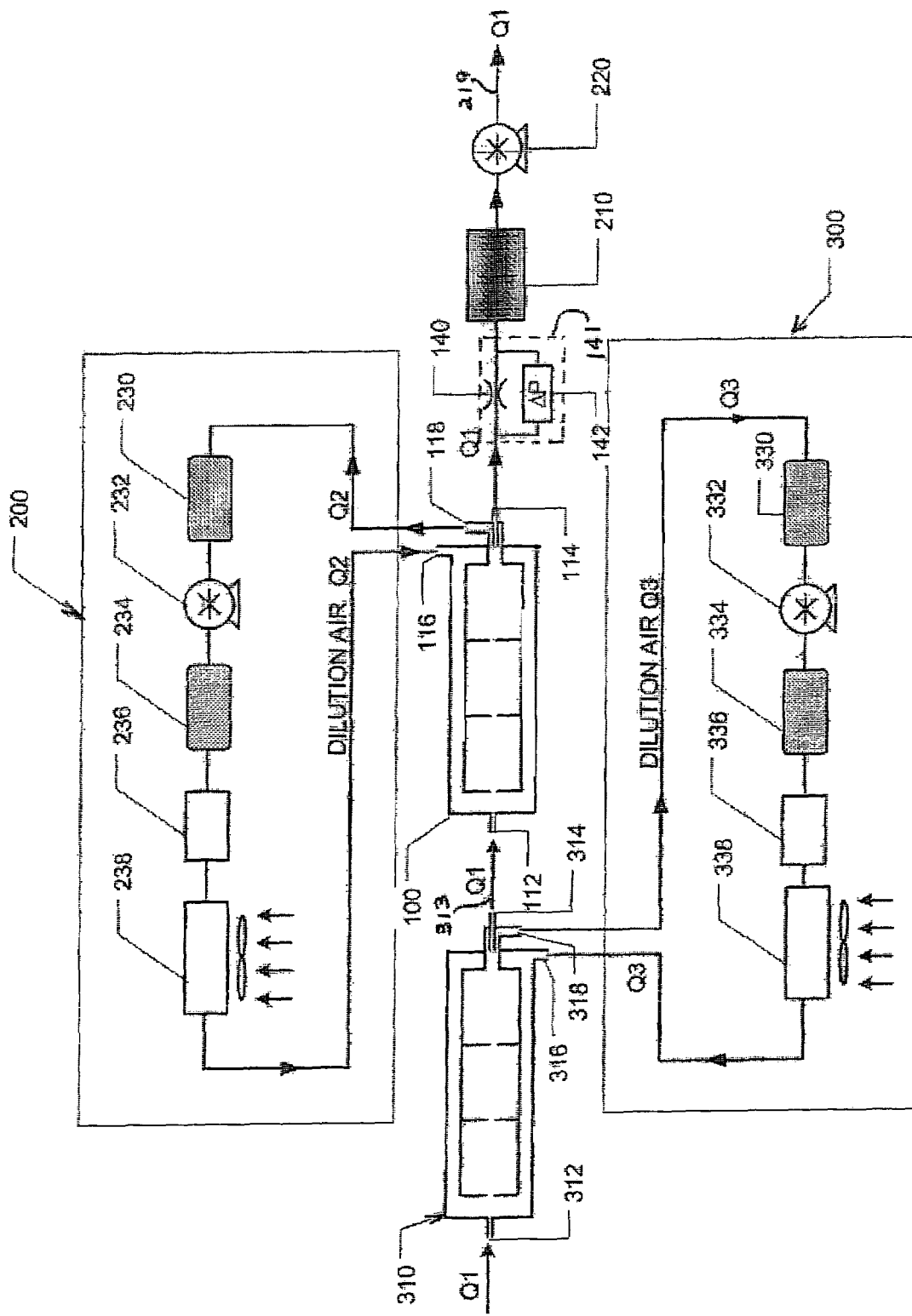
FIG. 4 is a schematic diagram depicting a two-stage serial diluter with two single 3-stage turbulent jet diluters connected in series, each provided with its own recirculating air flow system, drawing sample from the inlet and delivering a diluted sample at the exit at the same flow rate to a CPC for particle counting at a lower concentration.

FIG. 4 shows a system for particle measurement using two diluters 310 and 100 positioned in series such that the sample aerosol stream runs through both diluters, each diluter having its own recirculating flow system to supply clean air for dilution as previously described with respect to diluter 100 illustrated in FIG. 3. The system illustrated in FIG. 4 is essentially the system of FIG. 3 but with the additional diluter 310 to provide an additional stage of dilution.

The sample flow rate in the system of FIG. 4 is also maintained by the pump 220, drawing sample aerosol flow at a rate of Q1 through inlet 312 of diluter 310, providing a diluted sample flow 313 at the sample exit 314 also at Q1. The diluted sample 313 then flows into the inlet of the diluter 100, out of its sample outlet at 114, further diluted in concentration, then through the flow sensor 141 comprised of restriction 140 and the differential pressure gage 142, and into the CPC 210 for particle counting by the CPC. The flow 219 is then exhausted by pump 220. The sample flow rate in and out of each of the two diluters 310 and 100 are all at the same flow rate Q1 as indicated in FIG. 4.

The clean air for diluter 310 is drawn by pump 332 from diluter 310 through its excess aerosol outlet at 318, then through filters 330 and 334, flow sensor 336 and cooler 338 before the air is returned as clean air for dilution through inlet 318 of diluter 310 which is upstream from where it was withdrawn. The dilution flow rate Q3 is adjustable by adjusting the speed of pump 332 or by keeping the pump speed constant and adjusting the flow with a manual or automatic flow throttling valve (not shown).

The dilution factor, DF, i.e. the factor by which the aerosol concentration is diluted by a dilution system, is $$DF = \frac{Q2+Q1}{Q1}$$

for the single stage diluter system shown in FIG. 3, where (Q2+Q1) is the total flow through the diluter, Q1 is the sample flow and Q2 is the dilution flow, i.e. the recirculating air flow maintained by pump 232. For the two-stage serial diluter shown in FIG. 4, the dilution factor is $$DF = \left(\frac{Q2+Q1}{Q1}\right)\left(\frac{Q3+Q1}{Q1}\right)$$

For instance, if Q1=0.3 lpm, and Q2=29.70 lpm, the single diluter system of FIG. 3 will have a dilution factor of $$DF = \left(\frac{Q2+Q1}{Q1}\right) = \frac{30}{0.3} = 100$$

For the two stage diluter of FIG. 4, if additionally Q3=29.70 lpm, the dilution factor is then $$DF = \left(\frac{Q2+Q1}{Q1}\right)\left(\frac{Q3+Q1}{Q1}\right) = (100)(100) = 10,000$$

This example shows that a very large dilution factor can be achieved by using a suitable number of dilution stages. Since all the flow rates are easily adjusted by electrical or electronic means over a wide range of values, the system is also amenable to rapid user-adjustable control to meet the individual dilution needs of the user.

Figure 5:
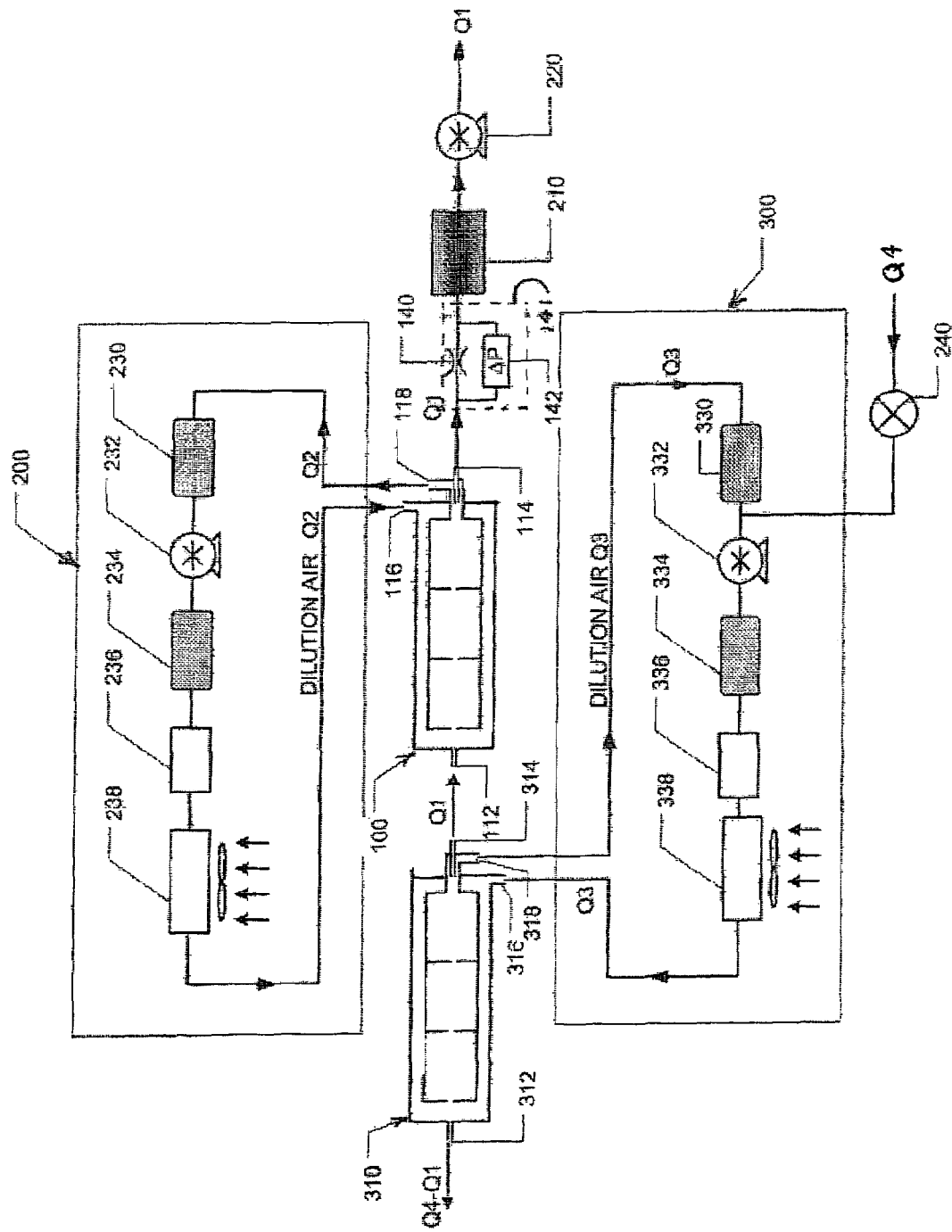
FIG. 5 is a schematic diagram depicting a diluter with a solenoid valve to provide clean purge air flowing through the sampling inlet in the reverse direction during standby.

FIG. 5 shows an inlet purge system that can be used with the diluter 310 to provide clean purge air through sample inlet 312. A solenoid valve 240 connected to system 300 is normally closed during sampling for particle measurement. When the system is on standby when no measurement is made, valve 240 can be opened to allow excess air from outside to be drawn by pump 332 into the system. The excess air, at a flow rate of Q4, is filtered by filter 334 and then appears as clean air in the diluter 310 at its inlet 312. If Q4 is larger than Q1, the difference, Q4−Q1, will appear as a reverse clean air flowing out of the inlet 112 in the reverse direction as a purge flow. For measuring high concentration aerosols, such as the exhaust particulates from a Diesel engine, this clean purge airflow can be used effectively during standby to keep the high concentration aerosol from entering the system, thereby preventing the system from being contaminated by particles. The purge flow greatly reduces frequency of maintenance that would otherwise be required. Aerosol sampling and particle counting can resume by simply closing valve 240.

Although the present invention has been described with reference to preferred embodiments, workers skilled in the art will recognize that changes may be made in form and detail without departing from the spirit and scope of the invention.

The invention claimed is:

1. An apparatus for detecting particles in an aerosol, the apparatus comprising:
   a diluter for diluting the concentration of particles in a sample aerosol stream by mixing the aerosol stream with a clean gas stream substantially free of particulate contaminants to form a diluted aerosol stream with a portion of the diluted aerosol stream used to form the clean gas stream; and
   a sensor for detecting particles in the diluted aerosol stream by vapor condensation, droplet growth and optical detection.

2. The apparatus of claim 1 wherein the diluter has a flow path for drawing the portion of the diluted aerosol stream, removing particles from the portion to form the clean gas stream.

3. The apparatus of claim 2 including a pump for drawing the portion from the diluted aerosol stream.

4. The apparatus of claim 3 including at least one filter for removing particles from the portion of the dilution aerosol stream drawn by the pump.

5. The apparatus of claim 2 including a cooling element for removing heat from the portion of the diluted aerosol stream drawn by the pump.

6. The apparatus of claim 2 including at least one additional diluter connected in series with the diluter such that the sample aerosol stream would flow through all diluters and each diluter having a discrete clean air path for progressively diluting the sample aerosol stream.

7. The apparatus of claim 1 wherein the diluter includes an inlet for the sample aerosol stream to enter, an inlet for the clean gas stream to enter and mix with the sample aerosol stream to form the diluted aerosol stream, an outlet for the diluted aerosol stream to exit, a mechanism for drawing a portion of the diluted aerosol stream from the exit, removing particles from the drawn portion, and returning the drawn portion as the clean gas stream to the diluter through the clean gas inlet.

8. The apparatus of claim 7 and further including at least one diluter connected in series with the diluter for progressively diluting the sample aerosol stream from one diluter to the next diluter downstream.

9. The apparatus of claim 1 wherein the diluter and sensor are disposed in a common housing.

10. A method for detecting particles in an aerosol stream, the method comprising:
    providing a diluter for diluting a concentration of particles in an aerosol stream to produce a diluted aerosol stream by mixing the aerosol stream with a clean gas stream;
    drawing a portion of the diluted aerosol stream to form the clean gas stream; and
    detecting particles in the diluted aerosol stream by vapor condensation, droplet growth and optical detection.

11. The method of claim 10 and further comprising:
    filtering the portion so drawn to form the clean gas stream.

12. The method of claim 11 wherein the portion of the diluted aerosol stream is drawn by a pump.

13. The method of claim 12 and further comprises:
    cooling the clean air stream.

14. The method of claim 13 and further comprising:
    providing two or more diluters fluidly connected in series such that the aerosol stream flows through all of the diluters to progressively dilute the aerosol streams.

15. The method of claim 14 and further comprising:
    drawing a portion from the diluted aerosol stream in each diluter.

16. The method of claim 15 and further comprising:
    turbulently mixing the aerosol stream through a restriction.

17. The method of claim 16 and further comprising:
    drawing a portion of the diluted aerosol stream downstream of the restriction,
    filtering and introduced the portion as the clean gas stream for diluting the aerosol stream.

18. The method of claim 17 and providing at least one of the diluters with more than one restriction, the restrictions being positioned downstream in series in a spaced apart relationship and being sized to create turbulent flow.

19. The method of claim 18 and further comprising drawing the aerosol stream through the restriction with a pump.

* * * * *